United States Patent
Jandhyala et al.

(10) Patent No.: US 11,732,579 B2
(45) Date of Patent: Aug. 22, 2023

(54) METHOD TO TAILOR CEMENT PROPERTIES AND OPTIMIZE INJECTION SCHEDULE FOR NEAR WELLBORE INTEGRITY IN CARBON STORAGE/INJECTION WELLS

(71) Applicant: Halliburton Energy Services, Inc., Houston, TX (US)

(72) Inventors: Siva Rama Krishna Jandhyala, Houston, TX (US); Katherine Evans, Abingdon (GB); Florence Mazouzi, Abingdon (GB); Kalyan Saikia, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 55 days.

(21) Appl. No.: 17/552,643

(22) Filed: Dec. 16, 2021

(65) Prior Publication Data
US 2023/0112008 A1  Apr. 13, 2023

Related U.S. Application Data

(60) Provisional application No. 63/254,322, filed on Oct. 11, 2021.

(51) Int. Cl.
*E21B 49/00* (2006.01)
*C09K 8/42* (2006.01)
(Continued)

(52) U.S. Cl.
CPC .............. *E21B 49/006* (2013.01); *C09K 8/42* (2013.01); *E21B 49/003* (2013.01);
(Continued)

(58) Field of Classification Search
CPC .... E21B 49/003; E21B 49/005; E21B 49/006; G01N 33/383; G06Q 50/02; C09K 8/42
See application file for complete search history.

(56) References Cited

U.S. PATENT DOCUMENTS

10,060,218 B2 * 8/2018 Jandhyala ................ G01V 1/40
10,364,643 B2 * 7/2019 Jandhyala ................ C09K 8/40
(Continued)

FOREIGN PATENT DOCUMENTS

EP  2309259 A1  10/2009

OTHER PUBLICATIONS

Sobolik et al. "Geomechanical Modeling to Predict Wellbore Stresses and Strains for the Desgin of Wellbore Seal Repair Materials for Use at a CO2 Injection Site" ARMA 15-290 (Year: 2015).*
(Continued)

*Primary Examiner* — John Fitzgerald
(74) *Attorney, Agent, or Firm* — Conley Rose, P.C.; Rodney B. Carroll (57) ABSTRACT

A method of designing a cement blend for a wellbore isolation barrier based on the analysis of a stress state of the wellbore isolation barrier from the injection of $CO_2$ into a porous formation. The analysis software may determine an optimized cement blend for a future $CO_2$ injection schedule. The analysis software may determine a current near wellbore stress state for a current $CO_2$ injection schedule. The analysis software may optimize a $CO_2$ injection schedule based on the analysis of a future near wellbore stress state of the wellbore isolation barrier. The near wellbore stress state of the isolation barrier may be determined by at least one model accessed by the analysis software. The inputs into the model comprise periodic $CO_2$ injection pressure and flow-rate datasets, cement properties, and formation properties.

21 Claims, 6 Drawing Sheets

(51) Int. Cl.
*G01N 33/38* (2006.01)
*G06Q 50/02* (2012.01)
(52) U.S. Cl.
CPC ......... *E21B 49/005* (2013.01); *G01N 33/383* (2013.01); *G06Q 50/02* (2013.01)

(56) References Cited

U.S. PATENT DOCUMENTS

| | | | |
|---|---|---|---|
| 10,564,080 | B2* | 2/2020 | Ju .......................... G01N 3/12 |
| 10,613,250 | B2* | 4/2020 | Prioul .................. G01V 99/005 |
| 2012/0206144 | A1* | 8/2012 | Barlet-Gouedard ........................ G01N 33/383 324/347 |
| 2018/0209267 | A1* | 7/2018 | Shen ................... E21B 41/0057 |
| 2020/0284945 | A1 | 9/2020 | Khan et al. |
| 2020/0332655 | A1* | 10/2020 | Hu ......................... E21B 49/008 |
| 2022/0010668 | A1* | 1/2022 | Vargo, Jr. .............. E21B 47/113 |
| 2023/0055082 | A1* | 2/2023 | Jandhyala ................ E21B 33/14 |

OTHER PUBLICATIONS

Nabih et al. "Stochastic Life Cycle Approach to Assess Wellbore Integrity for CO2 Geological Storage" SPE-170183-MS (Year: 2014).*

Chartier et al. "Peformance Characterization and Optimization of Cement Systems for Thermally Stimulated Wells" SPE-174493-MS (Year: 2015).*

Foreign Communication from Related Application—International Search Report and Written Opinion of the International Searching Authority, International Application No. PCT/US2022/032293, dated Sep. 23, 2022, 10 pages.

Aursand, Peter et al, "Well integrity for CO2 injection from ships: Simulation of the effect of flow and material parameters on thermal stresses," International Journal of Greenhouse Gas Control, 2017, pp. 130-141, vol. 62, Elsevier Ltd.

Roy, Pratanu et al, "Effect of thermal stress on wellbore integrity during CO2 injection," International Journal of Greenhouse Gas Control, 2018, pp. 14-26, vol. 77, Elsevier Ltd.

Asamoto, Shingo et al, "Well integrity assessment for CO2 injection: A numerical case study on thermomechanical behavior in downhole CO2 environments," International Journal for Computer-Aided Engineering and Software, 2013, pp. 842-853, vol. 30, No. 6, Emerald Group Publishing Limited.

Kim, Kiseok et al., "CO2 Injection Effect on Geomechanical and Flow Properties of Calcite-Rich Reservoirs," Fluids, Sep. 14, 2018, vol. 3, No. 66, 17 pages, MDPI.

Abdulqader Al-Ameri, Wahbi et al., "Long-Term Effects of CO2 Sequestration on Rock Mechanical Properties," Journal of Energy Resources Technology, Jan. 2016, vol. 138, pp. 1-9, ASME.

Aman, Michael et al., "CO2-Induced Chemo-Mechanical Alteration in Reservoir Rocks Assessed via Batch Reaction Experiments and Scratch Testing," Greenhouse Gases: Science and Technology, Sep. 22, 2017, vol. 8, No. 1, 36 pages, Society of Chemical Industry.

Espinoza, D. Nicholas et al., "CO2 charged brines changed rock strength and stiffness at Crystal Geyser, Utah: Implications for leaking subsurface CO2 storage reservoirs," International Journal of Greenhouse Gas Control, vol. 73, No. C, 38 pages, Elsevier, Jun. 1, 2018.

Ceyhan, Ismail et al., "Carbon Dioxide, Geochemical, and Rate-of-Dissolution Simulation for Deep Storage Environments," SPE International Symposium on Oilfield Chemistry, Apr. 2011, pp. 1-17, Society of Petroleum Engineers.

* cited by examiner

METHOD TO TAILOR CEMENT PROPERTIES AND OPTIMIZE INJECTION SCHEDULE FOR NEAR WELLBORE INTEGRITY IN CARBON STORAGE/INJECTION WELLS

CROSS-REFERENCE TO RELATED APPLICATIONS

This application claims priority under 35 U.S.C. § 119(e) to U.S. Provisional Patent Application No. 63/254,322 filed on Oct. 11, 2021 and entitled "Method to Tailor Cement Properties and Optimize Injection Schedule for Near Wellbore Integrity in Carbon Storage Wells," the disclosure of which is hereby incorporated herein by reference in its entirety.

BACKGROUND

In oil and gas wells a primary purpose of a barrier composition such as cement or a sealant is to isolate the formation fluids between zones, also referred to as zonal isolation and zonal isolation barriers. Cement is also used to support the metal casing lining the well, and the cement provides a barrier to prevent the fluids from damaging the casing and to prevent fluid migration along the casing.

Typically an oil well is drilled to a desired depth with a drill bit and mud fluid system. A metal pipe (e.g., casing, liner, etc.) is lowered into the drilled well to prevent collapse of the drilled formation. Cement is placed between the casing and formation with a primary cementing operation.

A primary cementing operation pumps a cement blend tailored for the environmental conditions of the wellbore. The primary cementing operation may utilize specialized pumping equipment on the drilling rig or transported to the drilling rig. The primary cementing operation may utilize various specialized downhole equipment such as wipers, darts, float shoes, and casing centralizers. The cement is typically pumped down the casing and back up into the annular space between the casing and formation.

Geologic storage of carbon dioxide ($CO_2$) typically utilizes a depleted oil or gas field that are no longer economic for oil and gas production. The depleted oil and gas fields can comprise reservoirs with desirable formation properties for the successful storage of $CO_2$. The $CO_2$ can be compressed and pumped into these depleted reservoirs through the cased and cemented wellbores. The injection of $CO_2$ can be tailored to maximize penetration of the $CO_2$ into the formation. The $CO_2$ may react with the formation and cement nearest the casing. A method of optimizing the cement blend and $CO_2$ injection schedule within the depleted oil and gas formation is desirable.

Monitoring of the injection of $CO_2$ into each zone of a wellbore is desirable. A production company may change the injection rate into a zone based on a change in the wellbore environment. Furthermore, monitoring of the barrier (e.g., cement or sealant) is useful to ensure continued zonal isolation during the operational life of the well.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The long term effectiveness of well barriers (e.g., cement, sealant compositions, or rock) in isolating one or more injection wellbores has long been an area of interest. Barriers made of Portland cement and non-Portland cement may change over time due to many environmental factors in a wellbore such as temperature, pressure, and corrosive fluids. In addition to environmental factors, changes in injection rates, formation pressures, well shut-ins, and well simulation may also change a cement well barrier with the additional stress applied. For example, a well shut-in may change the bottom hole temperature of a well and the axial loading of the wellbore. These changes in wellbore environment may lead to a well barrier failure. A well barrier failure of a carbon dioxide storage well may be prohibitively costly to repair. Early detection of a cement barrier failure may help an operator or well owner diagnose the cause of the barrier failure and potentially allow changes that would prevent the failure and prolong the life of the well.

In some embodiments, a cement blend can be designed based on predicted $CO_2$ injection rates. The evaluation software can access a database of wellbore data comprising geologic formation composition, porosity, depth, temperature, mechanical properties, and other environmental data to model the stress state of a cement blend based on predicted $CO_2$ injection rates.

In some embodiments, a $CO_2$ injection schedule for an existing wellsite can be designed with the objective of limiting the near wellbore stress state levels. The evaluation software can calculate a stress state of the cement well barrier based on the $CO_2$ injection schedule. In an example, a depleted oil well can be utilized as a $CO_2$ injection well. In another scenario, an existing oil well can be utilized for enhanced oil recovery as a $CO_2$ injection well.

In some embodiments, the cement well barrier may be modeled with one or more modeling applications to determine a current cement barrier stress level and a future well barrier stress level. Well barrier modeling can utilize temperature, pressure, material properties of wellbore materials (e.g., rock and/or cement), applied external loads, applied internal loads, and $CO_2$ injection rates from a given well to analyze and report the current state of the barrier and/or a future state of the barrier. The well barrier modeling applications can utilize computational fluid dynamics (CFD) modeling, geochemical modeling, rock mechanical model, and cement mechanical model to model a future state based on the injection rate of $CO_2$ and the downhole environment changes from the dissolution of minerals within the formation and reaction of $CO_2$ with set cement. The well barrier evaluation application can model a current state and a future state based on a cement blend utilized during wellbore construction. The well barrier evaluation application can update a user of the current state of the cement well barrier and its ability to continue to act as a barrier for $CO_2$ injection and $CO_2$ storage for the life of the well.

The pressure, temperature, and flow rate data can be provided by equipment sensors or based on data from offset wells. The sensor data can be transmitted to the evaluation software. The data from the sensors can be transmitted wirelessly by satellite or cellular service.

The evaluation software can access sensor data stored on a server periodically to evaluate the current state of the well barrier. The evaluation software can determine a current stress state then compare the current stress state to threshold value. The evaluation software can alert a user if the current stress state exceeds a threshold value. The evaluation software can send a report to storage if the current stress state is below the threshold value.

A user can transmit information of future applied loads (e.g., pressure, temperature, flow rate data, or combinations thereof) to the evaluation software to determine potential changes in the mechanical properties of rock and/or cement and a subsequent future applied stress state. The evaluation software can determine a future stress state by applying a future stress to the current stress state. The software can generate a report showing the future stress state and alert the user if the future applied stress state exceeds a threshold value.

Disclosed herein is a method of evaluating a current stress state and future stress state for a cement well barrier. The future stress state can be used to avoid future well operations that would damage the cement well barrier. The future stress state can be used to predict future cement well barrier damage from injection conditions. The future stress state can be used to alert users of a change to the current stress state of the cement well barrier.

Figure 1:
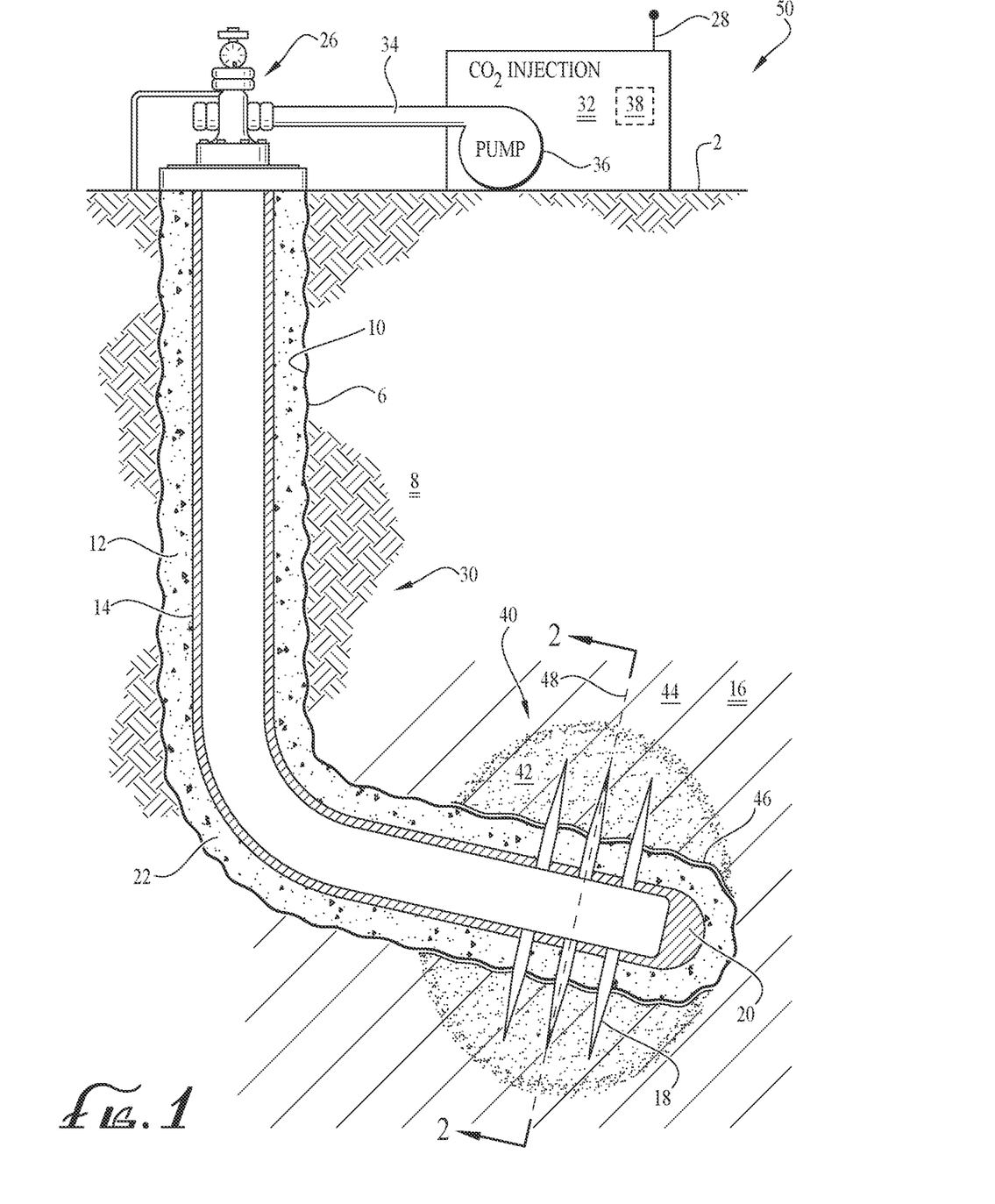
FIG. 1 is a cut-away illustration of an embodiment of a well system.

Turning now to FIG. 1, illustrated is a wellbore monitoring environment 50 that can be utilized to evaluate the wellbore isolation barrier. In some embodiments, the wellbore 6 can be drilled into the subterranean formation 8 using any suitable drilling technique and can extend in a substantially vertical direction away from the earth's surface. At some point in the wellbore 6, the vertical wellbore portion can transition into a substantially horizontal wellbore portion. In some embodiments, the wellbore 6 can be completed by cementing a casing string 14 within the wellbore 6 along all or a portion thereof. The cement 12 can be pumped down the casing 14, out a float shoe 20 (or other suitable primary cementing equipment), and into the annular space 22 between the casing string 14 and the inner surface 10 of the wellbore 6. A wellhead 26 can anchor the casing string 14, also called casing, at surface 2 and fluidically connect surface equipment to the wellbore 6. In other embodiments, however, the casing string 14 may be omitted from all or a portion of the wellbore 6 and the principles of the present disclosure can equally apply to an "open-hole" environment. In still other embodiments, however, the primary cementing equipment 20 at the end of the casing string 14 can be drilled out and a liner can be added to extend the length of the wellbore 6. In some embodiments, the casing string 14 may be referred to as a liner or a liner string.

The cement 12 can be Portland cement or a blend of Portland cement with various additives to tailor the cement for the wellbore environment. For example, retarders or accelerators can be added to the cement slurry to slow down or speed up the curing process. In some embodiments, the cement 12 can be or include a polymer designed for high temperatures. In some embodiments, the cement 12 can be cement blend designed to resist $CO_2$ corrosion. In some embodiments, the cement 12 can have additives such as expandable elastomer particles or nanoparticles.

The cement 12 placed in the annular space 22 between the casing 14 and the wellbore 6 can cure (harden) to form a wellbore isolation barrier, also referred to as a barrier. The term wellbore isolation barrier may refer to Portland cement or a blend of Portland cement that has cured or hardened. The term wellbore isolation barrier can refer to a polymer that has cured or hardened.

The wellbore 6 can be drilled through the subterranean formation 8 to a porous formation 16 suitable for $CO_2$ storage. Porous formations, e.g., 16, typically have geologic characteristics conducive to production or injection including pores, permeability, desired mineralogy, and a strata of impermeable rock above the porous formation. The pores of the porous formation 16 can be millimeter sized voids generally filled with a displaceable reservoir fluid. The permeability of the porous formation 16 generally provides a fluidic connection within the pores to allow the displacement of fluids. The desired mineralogy of the porous formation 16 may provide a means for retention of $CO_2$ as will be disclosure further herein. The strata of impermeable rock, also called a cap rock, above the porous formation 16 can contain the $CO_2$ within the porous formation 16.

Perforations 18 in the casing 14 and cement 12 provide a fluidic connection between with interior of the casing 14 and the fluid in the porous formation 16. In some embodiments, the perforations 18 may be replaced by a downhole tool suitable for establishing a fluidic connection with the porous formation 16 such as a production sleeve.

In some embodiments, the porous formation 16 can be a depleted oil and gas formation. The wellbore 6 may have supported the production of hydrocarbons from the porous formation 16 until the production was no longer economical. In this scenario, the wellbore construction of the original production well may have installed the casing 14 and cement 12 into the wellbore 6. The existing casing 14 and/or cement 12 can be utilized for $CO_2$ injection.

In some embodiments, the existence of a depleted oil and gas formation may be known, but a suitable wellbore may not be available. A wellbore 6 may be drilled into a porous formation 16, e.g., the depleted oil and gas formation. The casing 14 and cement 12 may be designed for the injection of $CO_2$ as will be disclosed further herein.

In some embodiments, the porous formation 16 can be a known formation conducive to $CO_2$ injection. A wellbore 6 may be drilled into a porous formation 16 with desirable formation characteristics. The casing 14 and cement 12 may be designed for the injection of $CO_2$ as will be disclosed further herein.

In some embodiments, the casing 14 and cement 12 within the wellbore 6 can be configured for the injection of $CO_2$ into the porous formation 16 for the storage of $CO_2$. The injection rates (pressure and volume) of the $CO_2$ can be optimized for the long term storage of $CO_2$ within the porous formation 16.

In some embodiments, the casing 14 and cement 12 within the wellbore 6 can be configured for the injection of $CO_2$ for enhanced oil recovery. In this scenario, the $CO_2$ injected into the wellbore 6 can sweep, e.g., displace, the formation fluids, e.g., hydrocarbons, from the porous formation 16 to an offset well for production of the formation fluids. In some embodiments, two or more offset wells can produce formation fluids swept from the porous formation 16 by the $CO_2$ injected into the wellbore 6. In some embodiments, at least one offset well can produce formation fluids swept from the porous formation 16 by the $CO_2$ injected into two or more wellbores such as wellbore 6.

The wellbore monitoring environment 50 may include surface equipment for the injection of $CO_2$ into the porous formation 16. A $CO_2$ injection equipment 32 may fluidically connect to the wellbore 6 via a high pressure line 34. The $CO_2$ injection equipment 32 may include a supply of $CO_2$, at least one injection pump, e.g., pumping equipment 36, and a unit controller 38. The $CO_2$ injection equipment may include compressor equipment suitable to increase the pressure of the supply of $CO_2$. The pumping equipment 36 can regulate the volumetric flowrate and injection pressure of the $CO_2$ into the wellbore 6. The unit controller 38 can comprise a processor, a non-transitory memory, and a communication device 28. The unit controller 38 can communicatively connect to the pumping equipment 36 of the injection equipment 32 to direct the injection of $CO_2$ from the $CO_2$ supply. A plurality of sensors, e.g., pressure and flowrate sensors, can provide feedback to the unit controller 38. The communication device 28 can communicatively connect the unit controller 38 to one or more remote users as will be disclosed herein.

The sensors communicatively connected to the unit controller 38 can include equipment sensors, wellhead sensors, and downhole sensors. The equipment sensors for the injection equipment 32 may include pressure sensors and flowrate sensors. The wellhead sensors can include pressure sensors and flowrate sensors. The downhole sensors can include wellbore sensors 30 positioned within the annular space 22 between the casing 14 and the wellbore 6. The wellbore sensors 30 can include electronic sensors attached to the casing or injection tubing with a means for power and communication coupled to the unit controller via the wellhead 26. In some embodiments, the wellbore sensors can be wellbore cables containing distributed sensors such as fiber optic cables. In some embodiments, the wellbore sensors can be battery powered electronic sensors transmitting data via sonar, radio frequency, or audio telemetry.

The data gathered by the sensors can include stress, strain, flow rate, pressure, temperature, and acoustic data. The wellbore sensors can measure the stress and strain applied to the casing 14 with a strain bridge mounted onto the surface of the casing 14.

The $CO_2$ injection equipment 32 may deliver compressed $CO_2$ at a predetermined flowrate and pressure to the wellbore 6 via the wellhead 26. The injection rate, e.g., flowrate and pressure, of the $CO_2$ may be determined by a programmed schedule or communicated to the injection equipment 32 via the communication device 28.

The $CO_2$ injection rate delivered to the wellbore 6 by the injection equipment 32 may deliver the desired volume and pressure of $CO_2$ to the porous formation 16 via the perforations 18. The volume of compressed $CO_2$ can migrate into the porous formation 16. This migration can generally be visualized as a $CO_2$ plume 40. The porous formation 16 can comprise a reacted rock portion 42 and an unreacted rock portion 44. The reacted rock portion 42 may contain minerals that have reacted with the $CO_2$ to change the chemical composition of the minerals. The bond strength 46 at an interface between the cement 12 to the reacted rock portion 42 may be determined.

Although the wellbore monitoring environment 50 is illustrated as a wellsite on land, it is understood that the wellbore monitoring environment 50 can be offshore. The wellhead 26 can be any type of pressure containment equipment connected to the top of the casing string 14, such as a surface tree, production tree, subsea tree, lubricator connector, blowout preventer, or combination thereof. The wellhead 26 can be located on a production platform, a subsea location, a floating platform, or other structure and supports operations in the wellbore 6. In some cases, such as in an off-shore location, the wellhead 26 may be located on the sea floor while the injection equipment 32 can be located on a structure supported by piers extending downwards to a seabed or supported by columns sitting on hulls and/or pontoons that are ballasted below the water surface, which can be referred to as a semi-submersible platform or floating rig.

Figure 2:
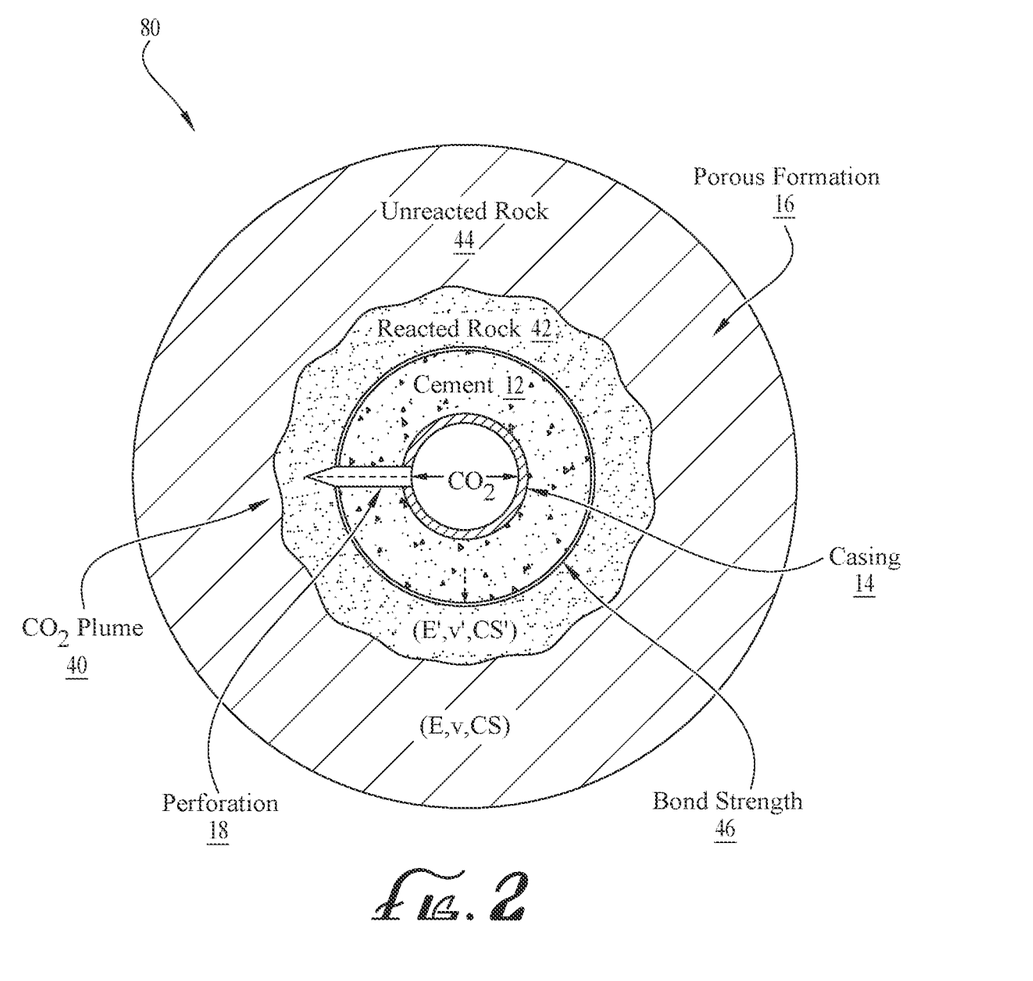
FIG. 2 is an illustration of a cross-sectional view of the wellbore isolation barrier the wellbore according to another embodiment of the disclosure.

Turning now to FIG. 2, a cross-sectional view 80 of the wellbore 6 along the line 48, shown in FIG. 1, is illustrated. The cross-sectional view 80 illustrates the $CO_2$ plume 40 extending outward from the casing 14 to penetrate the porous formation 16 as shown in FIG. 1. The $CO_2$ from the injection equipment 32 exits the casing 14 at perforations 18 that extend through the cement 12 to the reacted rock portion 42. The reacted rock portion 42 comprises the portion of the porous formation 16 in contact with the $CO_2$ plume 40. The reacted rock portion 42 may exhibit one or more chemical reactions with the $CO_2$ plume 40. The reacted rock portion 42 may exhibit structural changes due to the one or more chemical reactions within the reacted rock portion 42. The bond strength 46 at the interface between the cement 12 and the reacted rock portion 42 may be impacted due to the changes in mechanical properties of the cement 12, the reacted rock 42, or combinations thereof. Although the reacted rock portion 42 and unreacted rock portion 44 (and thus the $CO_2$ plume 40) are illustrated with a generally circular interface, it is understood that the shape of the interface may vary depending on the properties of the porous formation 16.

Figure 3:
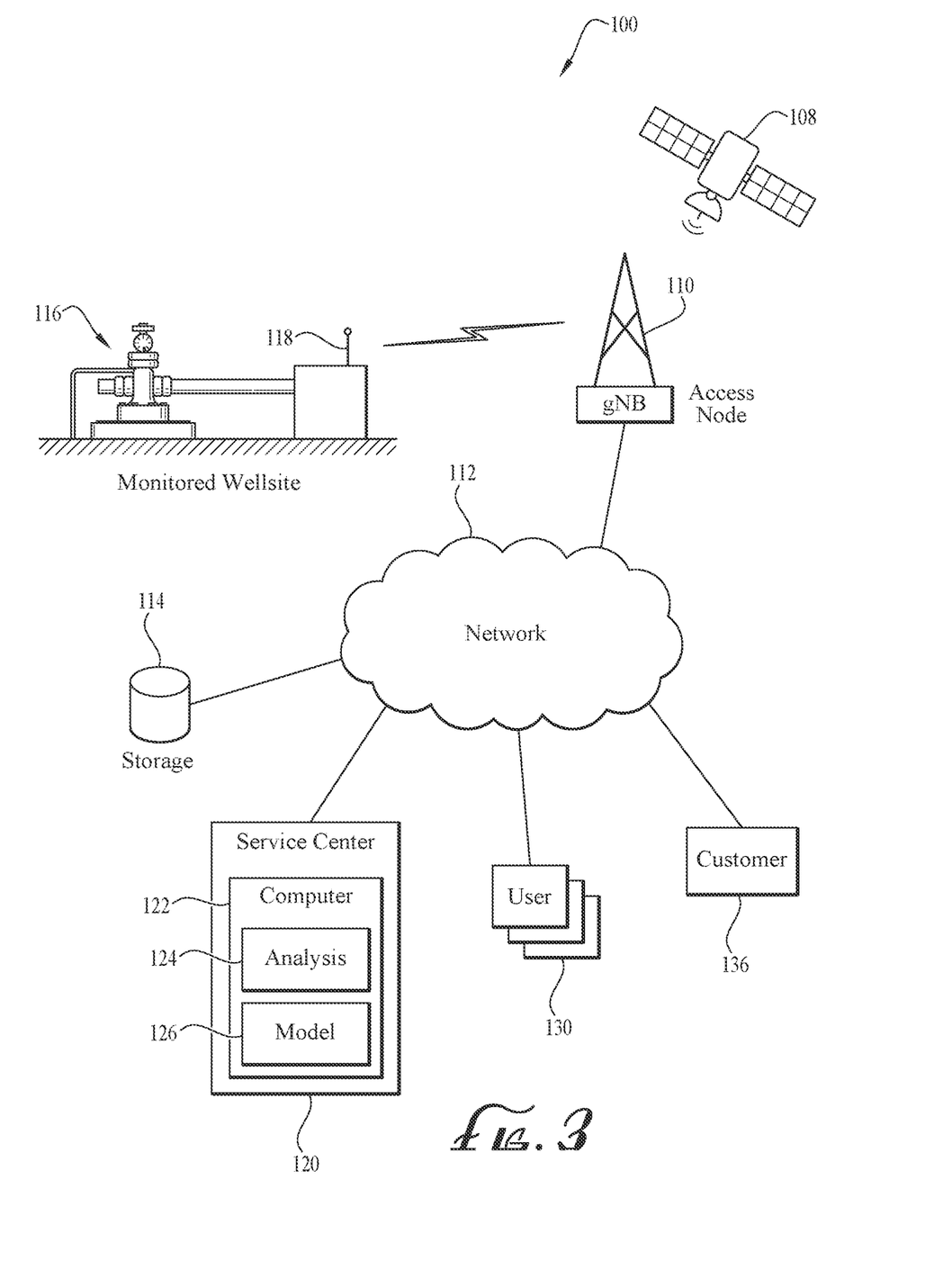
FIG. 3 is a block diagram of a communication system according to an embodiment of the disclosure.

Turning now to FIG. 3, a communication system 100 is described. The communication system 100 comprises a remote wellsite 116, a cellular site 110, a network 112, a storage computer 114, a computer system 122, a plurality of user devices 130, and a customer device 136. A remote wellsite 116, also referred to as a monitored wellsite, with a communication device 118 (e.g., communication device 28 of FIG. 1) can transmit via any suitable communication means (wired or wireless), for example wirelessly connect to a cellular site 110 to transmit data to a storage computer 114. The cellular site 110 can be communicatively connected to a network 112 that can include a 5G network, one or more public networks, one or more private networks, or a combination thereof. A portion of the internet can be included in the network 112. The storage computer 114 can be communicatively connected to the network 112. The service center 120 can have one or more servers and/or computer systems 122. An analysis application 124 can be executing on a computer system 122 in the service center 120.

A communication device 118 on a remote wellsite 116 can transmit data collected from the equipment sensors, wellhead sensors, and/or wellbore sensors to the storage computer 114. The communication device 118 can comprise a storage device and a data transmission device. The communication device 118 can wirelessly connect to the cellular site 110 continuously or at a predetermined schedule. In some embodiments, the communication device 118 can connect or attempt connection to the storage computer 114 via the cellular site 110 based on an established schedule. In some embodiments, the analysis application 124 can request the data from the communication device 118 based on an established schedule. The storage computer 114 can connect or attempt connection to the communication device 118 via cellular site 110 based on an established schedule. The communication device 118 can wirelessly connect to the network 112 via satellite communication 108.

A user device 130 can transfer a dataset from the storage computer 114 to an analysis application 124 executing on a computer system 122 in the service center 120. Alternatively, a dataset from the storage computer 114 can be transferred automatically or via a scheduler to an analysis application 124. The dataset can include the data collected from remote wellsite 116 over a designated time period. The analysis application 124 can determine a stress state for the time period selected of the cement isolation barrier. The user device 130 can compare the stress state of the cement isolation barrier to a threshold value and may alert a customer device 136. The user device 130 can transmit a report generated by the analysis application 124 to the customer device 136 via network 112.

Figure 4:
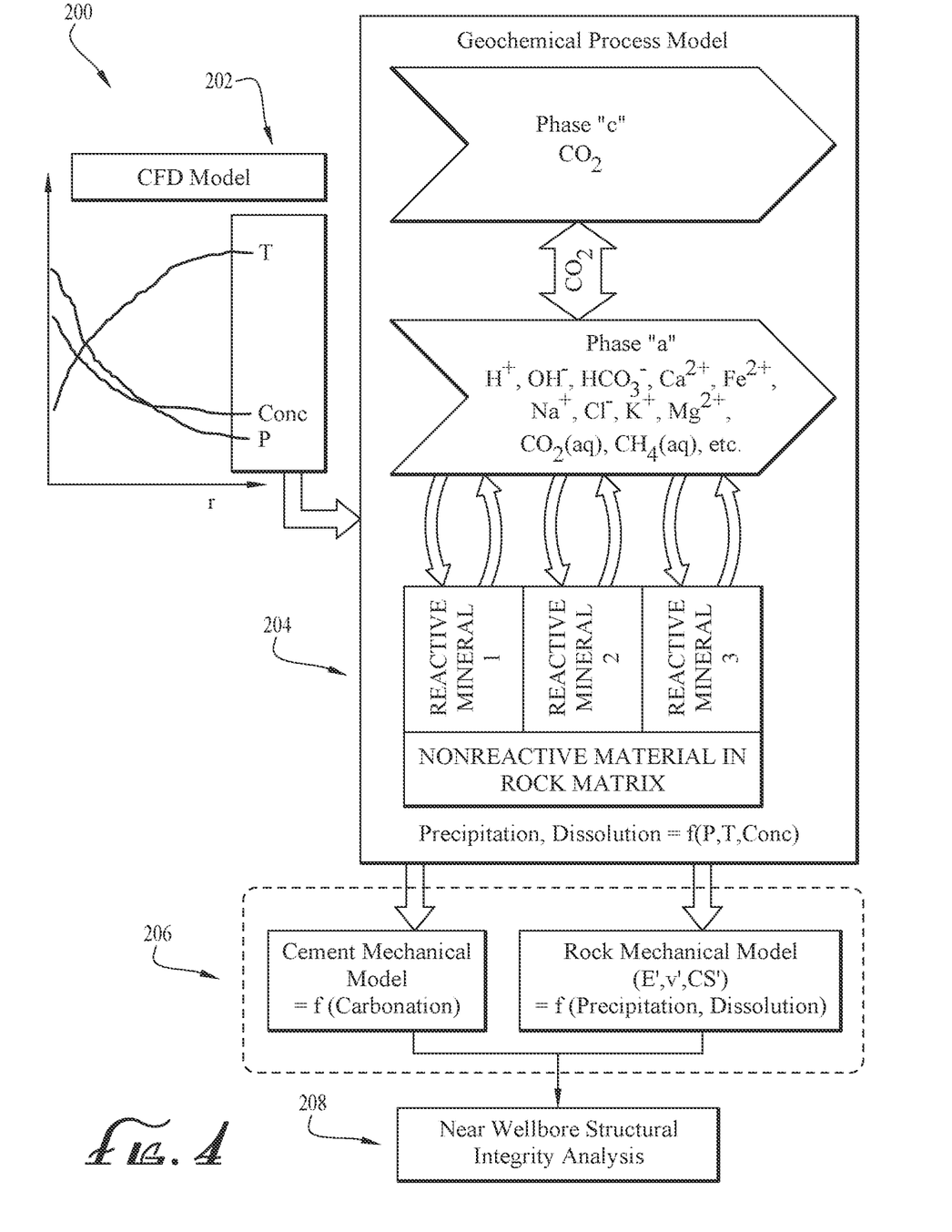
FIG. 4 is a logical flow diagram depicting an automated analysis application according to an embodiment of the disclosure.

Turning now to FIG. 4, a method 200 of evaluating a stress state of a wellbore isolation barrier with an analysis application is illustrated as a logic block diagram. The analysis application 124 of FIG. 3 comprises at least one model 126 to determine the stress state of the isolation barrier, e.g., cement 12 of FIG. 1. The analysis application 124 may include a computational fluid dynamics (CFD) model, a geochemical process model, a rock mechanical model, and a cement mechanical model. The analysis application 124 may determine the stress state of the isolation barrier, e.g., cement 12, with the results of at least one model 126, e.g., the cement mechanical model.

The method 200 comprises the following steps executing in an analysis application 124. At step 202, the $CO_2$ is pumped, also referred to as injected, into the wellbore 6 by the injection equipment 32 in supercritical conditions. The $CO_2$ can enter into the porous formation 16 via the perforation 18 and migrate through the pore space, forming a moving $CO_2$ plume 40. A multi-phase CFD model, e.g., model 126, that accounts for flow through porous medium, e.g., porous formation 16, and temperature evolution can be used to simulate the $CO_2$ migration process, e.g., plume 40, and the associated temperature and pressure changes. Outputs from the CFD model, e.g., model 126, are temperature, pressure, and concentration of $CO_2$ near the wellbore 6. These outputs when extracted at a specific distance from wellbore wall, e.g., wellbore 6 and/or interface of the bond strength 46, serve as inputs of modified loads to the near wellbore integrity analysis step.

At step 204, the values of pressure, temperature, and $CO_2$ concentration from step 202 form inputs to a Geochemical process model, e.g., model 126. In this model 126, two events occurring in the formation 16 are modeled. The first event includes can include $CO_2$ from the plume 40 dissolving in aqueous formation fluids, for example brine water. Dissolution of the plume 40 is governed by thermodynamics and phase equilibrium calculations. Ionic composition of the aqueous fluid, pressure, temperature, and $CO_2$ concentration govern this process. The second event includes the aqueous fluid triggering precipitation and/or dissolution of minerals in the rock, e.g., formation 16. The kinetics of this process, the second event, is governed by the chemical potential difference of various minerals between the formation fluid and the rock, e.g., formation 16. A model 126 can be used to describe this entire geochemical process. Outcome from this model can include the dissolution and precipitation of active rock minerals. In an alternative embodiment, the first model from step 202, e.g., the CFD model, and the second model from step 204, e.g., the geochemical process model, may be combined into a single model, e.g., model 126.

At step 206, the precipitation and dissolution events of step 204 modify the rock mineralogy and the cement composition and thus the mechanical properties. A rock mechanical model, e.g., model 126, can describe how mechanical properties evolve as a function of composition of the rock, e.g., formation 16. For example, a simple form of such model, e.g., model 126, is volume averages of mechanical properties of pure species.

$$YM = \Sigma_{i=1}^{N} V_i \times YM_i$$

For example, the effective Young's Modulus (YM) of rock can be obtained as volume fraction ($V_i$) weighted average of YM of individual rock mineral i (i.e., $YM_i$). The rock mechanical model can determine other elastic properties of the formation 16 based on volumetric averaging techniques. The model can determine the strength of the dissolving/precipitating rock using empirical equations or inputting the results of laboratory tests using reacted and unreacted cores.

Continuing with step 206, concurrent with the rock mechanical model previously described, a cement mechanical model, e.g., model 126, can describe how the mechanical properties of the cement, e.g., cement 12, change because of carbonation and bi-carbonation reactions. The cement and rock mechanical models, e.g., model 126, can also determine the bond strength 46 of the interface between cement and rock. The cement and rock mechanical models can determine a change and/or rate of change of the bond strength 46 due to the reaction of step 204. The cement and rock mechanical models can determine an evolution, e.g., rate of change, of the bond strength 46. In some scenarios, the output the CFD model from step 202 may be inputting directly into the cement mechanical model.

In some embodiments, step 204 may provide inputs to only one of the models of step 206. For example, the prior step (step 204) may provide inputs to the rock mechanical model but not the cement mechanical model. In another scenario, step 204 may provide inputs to the cement mechanical model but not the rock mechanical model. The analysis process of method 200 may not have the information available for inputs into both the rock mechanical model and the cement mechanical model.

In an alternative embodiment, the rock mechanical model from step 206 and the cement mechanical model from step 206 may be combined into a single model, e.g., model 126. In another alternative embodiment, the second model from step 204, e.g., the geochemical process model, and the third model from step 206, e.g., the rock mechanical model and/or the cement mechanical model, and may be combined into a single model, e.g., model 126. In still another alternative embodiment, the first model from step 202 (CFD model), the second model from step 204 (geochemical model), the third model from step 206 (cement mechanical model), the concurrent third model from step 206 (rock mechanical model), or combinations thereof may be combined into a single model, e.g., 206.

At step 208, a 'Near Wellbore Structural Integrity Analysis' process will utilize information coming from steps 202, 204, and 206 to determine a stress state. Temperature and pressure conditions inside the rock can be imported from step 202. Mechanical properties of cement and rock can be imported from step 206. Additional inputs related to the downhole environment and applied stress, for example external injection stress from inside the casing 14, can be an input. The Near Wellbore Structural Integrity Analysis process can include a thermo-structural analysis to determine one or more stress states near the wellbore 6. This stress state can be compared to the failure properties of rock (porous formation 16), cement 12, and casing 14 to assess the risk of loss in near wellbore integrity.

Steps 202 through 208 can be repeated for different $CO_2$ injection schedules and/or cement compositions, e.g., cement blends. The determination of the stress state near the wellbore can be used to determine an injection schedule, e.g., injection pressure and rate, and cement composition, e.g., cement blend, that minimizes the risk of loss in near wellbore integrity.

The method 200 can establish a computational connection of four events which can occur across different length and time scales. The method 200 can identify how, when and what type of information should be exchanged across these events without loss of accuracy or incurring a significant increase in computational capacity.

The present disclosure can provide a method of coupling four events, which can contribute to the evaluation of the risk of wellbore damage, comprising i) mass and heat transport during $CO_2$ plume migration (via step 202), ii) multi-phase reactions governed by thermodynamics and kinetics (via step 204), iii) mechanical property changes governed by composition variations in rock and cement (via step 206), and iv) near wellbore (NWB) analysis (via step 208) governed by laws of structural mechanics. Each event is described by one or more models, e.g., model 126. The last event (step 208), i.e., Near Wellbore Structural Integrity Analysis, can assess the magnitude of risk to wellbore damage during the described $CO_2$ injection/storage process. Each event comprises a model, for example analysis software, with an input, governing equations, time scale of relevance, and an output. The output of an event may form the input of one or more subsequent events.

Figure 5A:
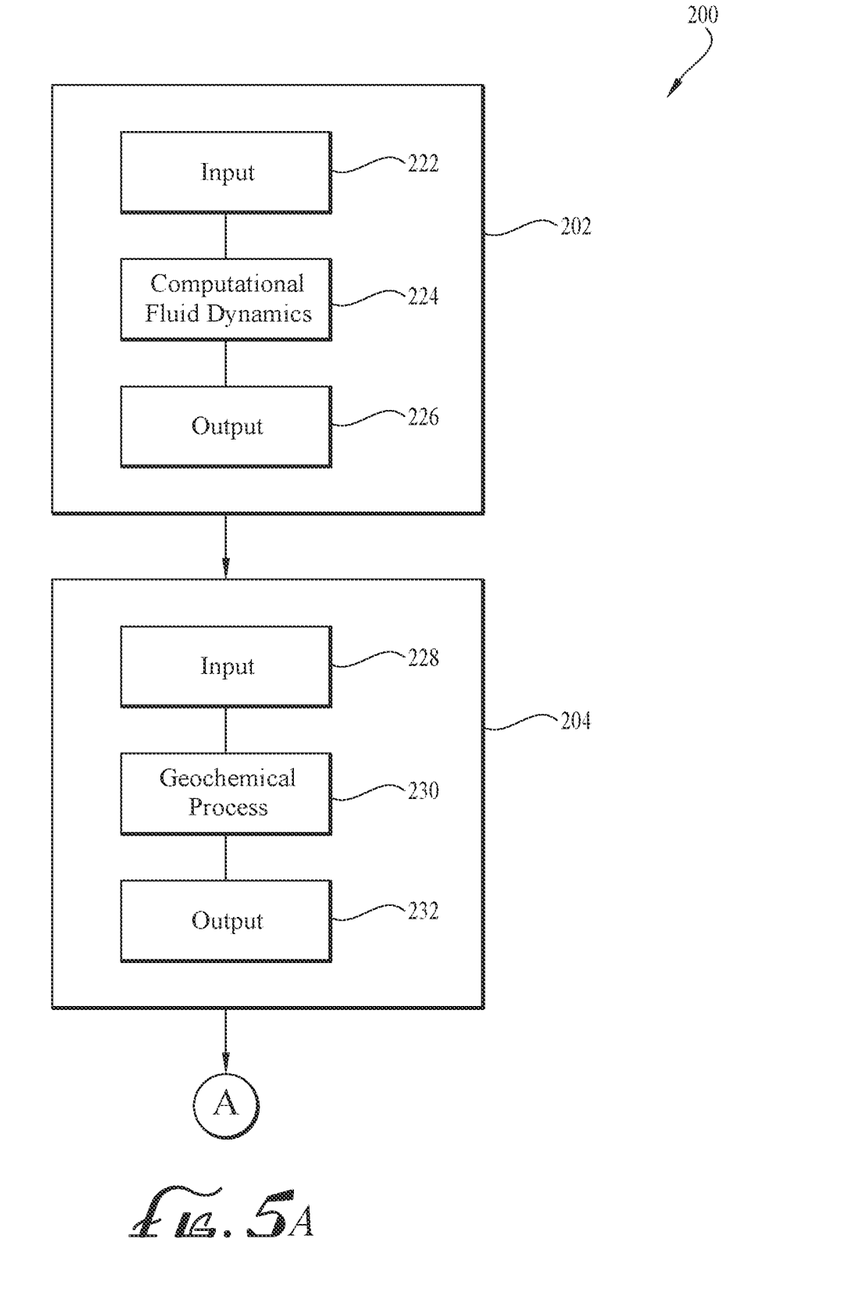
FIGS. 5A and 5B are an illustration of the logical flow diagram depicting an automated analysis application according to another embodiment of the disclosure.
Figure 5B:
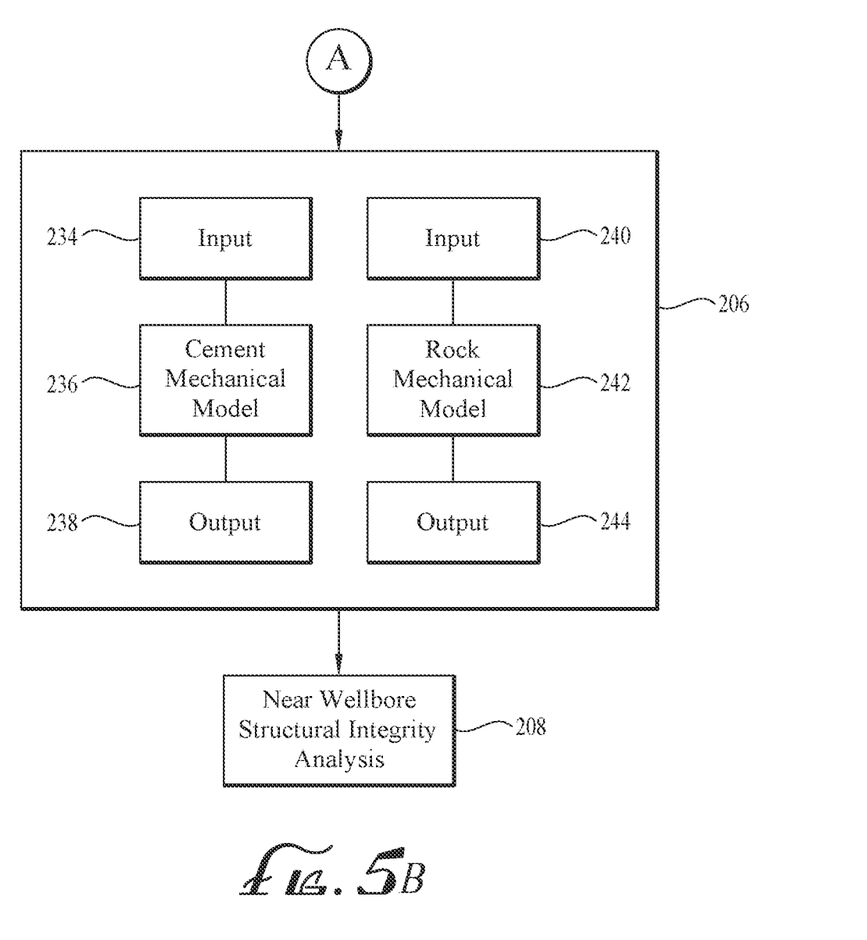

Turning now to FIG. 5A and FIG. 5B, the method 200 of evaluating a stress state of a wellbore isolation barrier with an analysis application 124 is illustrated as a logic block diagram. In some embodiments, the method 200 comprises the following steps executing in an analysis application 124. At step 202, the analysis application 124 of FIG. 3 can deliver input values 222 to the model 224, e.g., the CFD model, to determine the migration of the $CO_2$ plume 40 within the formation 16. The analysis application 124 can retrieve a plurality of datasets from the remote storage of communication device 118 on the remote wellsite 116. The datasets can include injection pressure and injection flowrate of the injection equipment 32. The analysis application 124 can input the datasets as input values 222 into one or more models 224. The model 224 can comprise a computational fluid dynamics (CFD) model. The model 224, e.g., CFD model, can determine the migration of $CO_2$ plume 40 for a given input of injection pressure, temperature, and downhole conditions. The model 224, e.g., CFD model, can calculate a basin scale analysis from which boundary conditions of near wellbore scale can be extracted. In an example, near wellbore can include a prescribed distance from the wellbore wall. Boundary conditions will be in the form of pore pressure, temperature and deformations in the rock. These form the 'modified loads' portion for near wellbore analysis. The CFD model 224 can determine output values 226 comprising a set of a pressure value, a temperature value, a $CO_2$ partial pressure value as a function of time and location within the porous formation 16.

At step 204, the input values 228 of the second model, e.g., model 230, can include the output values 226 of the first model, e.g., model 224. The analysis application 124 can transfer the outputs values 226 from the CFD model 224 to the geochemical model 230 as input values 228. The input values 228 may include the material properties of the porous formation 16. The geochemical model 230 can determine the precipitation and dissolution rates of the reactive part, e.g., minerals, of the porous formation 16 and wellbore isolation barrier, e.g., cement 12, from the pressure, temperature, and $CO_2$ partial pressure. Dissolution/Precipitation geochemical models may be based on equilibrium thermodynamics using different types of equations of state along with reaction kinetics involving different aqueous species. A model, e.g., model 230, can simulate the equilibrium state of $CO_2$, e.g., plume 40, in contact with aqueous (brine) phase present in rocks, e.g., formation 16. Further, the model 230 may describe the reaction between active rock minerals, e.g., formation 16, and the $CO_2$ dissolved brine. Reaction can be determined by a difference in chemical potential of various species between brine and rock and on the rate constants. Rate constants can be available in literature. An example of geochemical model can be found at SPE-141031-MS. The sequence of reactions can be a function of rock mineralogy. The geochemical model 230 can determine output values 232 comprising the precipitation and dissolution rates of the porous formation 16 and cement 12.

At step 206, the input values, e.g., input values 234, of the third model, e.g., model 236, can include the output values 232 of the second model, e.g., model 230. The analysis application 124 can transfer the outputs values 232 from the geochemical model 230 to the cement mechanical model 236 as input values 234 and rock mechanical model 242 as input values 240 to determine the near wellbore (NWB) rock and cement stress as a function of time. In some scenarios, the output values 232 of the second model (model 23) may provide inputs to either cement mechanical model 236 or rock mechanical model 242 but not both. The rock mechanical model 242 can calculate the changes to the mechanical properties of the porous formation 16. As a consequence of precipitation and dissolution, mechanical properties of rock and cement can change. A model 242 can describe the changes to these mechanical properties as a function of extent of carbonation based on wave measurements of reacted and unreacted cores or through destructive mechanical testing of reacted and unreacted rock cores. In some scenarios, the output the CFD model 224 from step 202 may be inputting directly into the cement mechanical model 236. The cement mechanical model 236 can determine output values 238 comprising the mechanical properties of the cement 12 as a function of time (i.e., extent of the reaction). The rock mechanical model 242 can determine output values 244 comprising the mechanical properties of the porous formation 16 as a function of time (i.e., extent of reaction).

At step 208, the input values of the analysis application 124 can include the output values, e.g., output values 238, of the third model, e.g., model 236. The analysis application 124 can retrieve the output values 238 comprising the cement mechanical properties from the model 236 and the output values 244 comprising the rock mechanical properties from the model 242. The analysis application 124 may perform a near wellbore integrity analysis using the time dependent properties of the cement 12 and porous formation 16. The analysis application 124 can capture the response of near wellbore based on changes to mechanical loads and changes to mechanical properties of rock, e.g., formation 16, and cement 12 during a carbon storage event. A determination of a future stress state of the wellbore isolation barrier, e.g., cement 12, can performed with inputs including a design cement blend to tailor a future cement 12, e.g., wellbore isolation barrier, properties and/or future injection schedule. The determination of a future stress state that is below a threshold value, e.g., cement mechanical properties, can optimize a future injection schedule such that the storage well integrity is preserved.

In some embodiments, the method of determining a near wellbore stress can be used to determine a cement blend for a future wellbore at a new wellsite.

Turning back to FIG. 3, a user device 130 can receive a request from a customer device 136 for a cement blend and/or an injection schedule for a remote wellsite 116. In some embodiments, the remote wellsite 116 may not be drilled nor completed. The customer request may include the design of a cement blend for the injection of $CO_2$ into the wellbore 6.

The user device 130 may design a cement blend for the remote wellsite 116 utilizing an analysis application 124 executing on a computer system 122 within a service center 120. The analysis application 124 may retrieve a first cement blend, the one or more customer inputs, and a first injection schedule from a storage computer 114. The injection schedule can comprise a future injection pressure and injection flowrate values for periodic carbon dioxide ($CO_2$) injection at the remote wellsite 116. The time frame for the periodic $CO_2$ injection may be minutes, hours, days, weeks, months, or combinations thereof.

The customer inputs may comprise a plurality of wellbore data and a plurality of customer design inputs. The customer design inputs may include the first cement blend, casing 14, primary cementing equipment 20, at least one downhole tool, or combinations thereof. The wellbore data for the future wellsite, e.g., remote wellsite 116, can include a wellbore location, a wellbore history, and a plurality of sensor data. The wellbore location comprises well names, a lease location, global positioning satellite (GPS) coordinates, an internal designation, or a combination thereof. The wellbore history can comprise a wellbore survey, a wellbore drilling path, a wellbore production fluid analysis, a wellbore drilling fluid, and a wellbore construction history. The plurality of sensor data can comprise a well logging dataset, wellbore production sample, and well control data.

Although the first cement blend, the customer inputs, and the injection schedule is disclosed as located on the storage computer 114, it is understood that the information may be located on the computer system 122, the user device 130, the customer device 136, the storage computer 114, or combinations thereof. The user device 130 may be communicatively coupled to the storage location, e.g., customer device 136, via the network 112, the cellular site 110, the satellite communication 108, or a combination thereof. Although the analysis application 124 is described as executing on a computer system 122, it is understood that the analysis application 124 may be executing on the storage computer 114, the user device 130, the customer device 136, a virtual computer system via a 5G network, a computer system 122, or a combination thereof.

The analysis application 124 may input a first set of inputs into a first model 126 comprising a computational fluid dynamics (CFD) model. The first set of inputs comprise the cement blend, the one or more customer inputs, the one or more injection schedule, or combinations thereof.

The analysis application 124 may receive the output of the first model 126, the CFD model, and input the first model output into a second model 126 comprising a geochemistry model.

The analysis application 124 may receive the output of the second model 126, the geochemistry model, and input the second model 126 output into a third model comprising a mechanical property model.

The analysis application 124 may receive the output of the third model 126, the mechanical property model, and determine a near wellbore stress state.

The analysis application 124 may compare a failure property of at least one of i) rock, ii) cement, iii) casing, iv) or combination thereof to the near wellbore stress state. The analysis application 124 may modify the cement blend, the injection schedule, or combination thereof in response to the near wellbore stress state exceeding at least one threshold of the failure property of at least one of i) rock, ii) cement, iii) casing, iv) or combination thereof.

If the analysis application 124 determines that the near wellbore stress state is below the threshold of the failure property, the analysis application 124 may generate the cement blend, the injection schedule, or combination thereof. The cement blend and injection schedule may be designated the designed cement blend and the designed injection schedule.

A service company can transport the designed cement blend and a plurality of cement pumping equipment to the wellsite in response to the output of the designed cement blend. The designed cement blend can be included in the cement placement procedure. The cement pumping equipment can comprise a mixing equipment, a pumping equipment, and a unit controller. The unit controller can comprise a processor, a non-transitory memory, and the cement placement procedure.

The cement pumping equipment can be fluidically connected to a wellbore. The unit controller can direct the cement pumping equipment to mix the designed cement blend and to pump the designed cement blend into the wellbore per the cement placement procedure.

In some embodiments, the method of determining a near wellbore stress state can be used to determine an injection schedule for an injection well. In this scenario, an existing wellsite can be used as an injection well. In another scenario, this method may be utilized for enhanced oil recovery.

Turning back to FIG. 3, a user device 130 can receive a request from a customer device 136 for a future injection schedule for a remote wellsite 116. In some embodiments, the remote wellsite 116 can comprise an existing wellsite including the cured cement blend, e.g., the isolation barrier, and the casing string 14 installed into the wellbore 6.

The user device 130 may design a future injection schedule for the remote wellsite 116 utilizing an analysis application 124 executing on a computer system 122 within a service center 120. The analysis application 124 may retrieve a one or more customer inputs and a first injection schedule from a storage computer 114. The first injection schedule can comprise future injection pressure values and injection flowrate values for periodic $CO_2$ injection at the remote wellsite 116. The time frame for the periodic $CO_2$ injection may be minutes, hours, days, weeks, months, or combinations thereof.

The customer inputs may include the cement blend of the isolation barrier and casing string 14 utilized to complete the wellbore 6 of the remote wellsite 116.

As previously described, the analysis application 124 may input the cement blend, the casing string 14, the one or more customer inputs, and the one or more injection schedule into a first model 126 comprising a CFD model.

As previously described, the analysis application 124 may process the outputs of a first model, e.g., CFD model, into a second, and third model. The analysis application 124 may calculate by a near wellbore stress state from the output of the third model.

If the analysis application 124 determines that the near wellbore stress state is below the threshold of the failure property, the analysis application 124 may generate the future injection schedule. The future injection schedule may be designated the design injection schedule.

The user device may transmit the design injection schedule to an $CO_2$ injection equipment 32 at the remote wellsite 116 in response to the output of the design injection schedule. The $CO_2$ injection equipment 32 comprises a $CO_2$ supply, a compression equipment, a pumping equipment 36, and a unit controller 38. The unit controller 38 can comprise a processor, a non-transitory memory, a communication device 28, and the design $CO_2$ injection schedule.

The $CO_2$ injection equipment 32 can fluidically connect to the wellbore 6 of the remote wellsite 116 via high pressure line 34. The unit controller 38 can direct the $CO_2$ injection per the $CO_2$ injection schedule to pump $CO_2$ into the wellbore per the $CO_2$ injection schedule.

In some embodiments, the method of determining a near wellbore stress state can be used to predict a future stress state from an injection schedule for an injection well. In this scenario, an existing wellsite may currently be utilized as an injection well.

Turning back to FIG. 3, a user device 130 can receive a request from a customer device 136 to change an injection schedule for a remote wellsite 116. In some embodiments, the remote wellsite 116 can comprise an existing wellsite including the cured cement blend, e.g., isolation barrier, and the casing string 14 installed into the wellbore 6.

The user device 130 may design a future injection schedule for the remote wellsite 116 utilizing an analysis application 124 executing on a computer system 122 within a service center 120. The analysis application 124 may retrieve a one or more customer inputs and a first injection schedule from a storage computer 114. The injection schedule can comprise future injection pressure and injection flowrate values for periodic $CO_2$ injection at the remote wellsite 116. The time frame for the periodic $CO_2$ injection may be minutes, hours, days, weeks, months, or combinations thereof.

The customer inputs may include the cement blend and casing string 14 utilized to complete the wellbore 6 of the remote wellsite 116.

In this embodiment, the analysis application 124 may retrieve a current near wellbore stress state that coincides with a current injection schedule for the remote wellsite 116.

As previously described, the analysis application 124 may input the cement blend, the casing string 14, the one or more customer inputs, and the one or more future injection schedule into a first model 126 comprising a CFD model.

As previously described, the analysis application 124 may process the outputs of a first model, e.g., CFD model, into a second, and third model. The analysis application 124 may calculate by a future near wellbore stress state from the output of the third model.

The analysis application 124 may compare the present near wellbore stress state to the future near wellbore stress state.

If the analysis application 124 determines that the future near wellbore stress state is below the threshold of the present near wellbore stress state, the analysis application 124 may generate the injection schedule. The injection schedule may be designated the designed injection schedule.

The user device 130 may transmit the design injection schedule to an $CO_2$ injection equipment 32 at the remote wellsite 116 in response to the output of the design injection schedule. The $CO_2$ injection equipment 32 comprises a $CO_2$ supply, a compression equipment, a pumping equipment 36, and a unit controller 38. The unit controller 38 can comprise the design $CO_2$ injection schedule.

The $CO_2$ injection equipment 32 can fluidically connect to the wellbore of the remote wellsite 116. The unit controller 38 can direct the $CO_2$ injection per the design injection schedule to pump $CO_2$ into the wellbore per the design injection schedule.

ADDITIONAL DISCLOSURE

The following are non-limiting, specific embodiments in accordance and with the present disclosure:

A first embodiment, which is a computer-implemented method of designing a wellbore isolation barrier, comprising inputting, by an analysis application, a first set of inputs into a first model, wherein the first model is a computational fluid dynamics (CFD) model, and wherein the first set of inputs comprises a cement blend, an one or more customer inputs, and an injection schedule, inputting, by the analysis application, a second set of inputs into a second model, wherein the second model is a geochemistry model, wherein the second set of inputs comprises a first output from the first model, inputting, by the analysis application, a third set of inputs into a third model, wherein the third model is a mechanical property model, wherein the third set of inputs comprises a second output from the second model, determining, by the analysis application, a near wellbore stress state from an input, wherein the inputs comprises a third output from the third model, the first output from the first model, a set of user inputs, or combination thereof, comparing, by the analysis application, a failure property of at least one of i) rock, ii) cement, iii) casing, iv) or combination thereof, to the near wellbore stress state, modifying, by the analysis application, the cement blend, the injection schedule, or combination thereof, in response to the near wellbore stress state exceeding at least one threshold of the failure property, and generating, by the analysis application, the cement blend, the injection schedule, or combination thereof in response to the threshold of the failure property exceeding the near wellbore stress state.

A second embodiment, which is the method of the first embodiment, further comprising retrieving, by the analysis application, the first set of inputs from a remote data source by a first communication method.

A third embodiment, which is the method of any of the first and the second embodiments, wherein the mechanical property model is a cement mechanical model, a rock mechanical model, or combination thereof.

A fourth embodiment, which is the method of and of the first through the third embodiments, wherein the injection schedule comprises periodic carbon dioxide ($CO_2$) injection pressure, temperature, and flowrate values, and wherein the one or more customer inputs comprise a plurality of wellbore data and a plurality of customer design inputs comprising a bill of materials and one or more construction plans.

A fifth embodiment, which is the method of the fourth embodiment, wherein the wellbore data comprises a wellbore location, a wellbore history, a plurality of sensor data, or combination thereof, wherein the wellbore location comprises well names, a lease location, global positioning satellite (GPS) coordinates, an internal designation, or combination thereof, wherein the wellbore history comprises a wellbore survey, a wellbore drilling path, a wellbore production fluid analysis, a wellbore drilling fluid, a wellbore construction history, or combination thereof, and wherein the plurality of sensor data comprises well logging, wellbore production sample, well control data, or combination thereof.

A sixth embodiment, which is the method of any of the first through the fifth embodiments, further comprising transporting the cement blend and a plurality of cement pumping equipment to a well site in response to an output of the cement blend, wherein the cement blend is included in a cement placement procedure, wherein the cement pumping equipment comprise a unit controller, connecting the cement pumping equipment to a wellbore via a wellhead, wherein the pumping equipment is fluidically connected to the wellbore, beginning the cement placement procedure by the unit controller, retrieving, by the unit controller, one or more datasets of periodic pumping data indicative of the cement placement procedure, mixing a cement slurry comprising the cement blend, by the cement pumping equipment, per the cement placement procedure, and pumping the cement slurry per the cement placement procedure into the wellbore.

A seventh embodiment, which is the method of any of the first through the sixth embodiments, further comprising evaluating, by the analysis application, the near wellbore stress state for a wellbore isolation barrier to maintain at least one mechanical properties of i) a porous formation, ii) the wellbore isolation barrier, iii) the casing, or iv) combinations thereof by reducing the near wellbore stress state below a threshold by modifying an application of the injection schedule by an injection equipment.

An eighth embodiment, which is a computer-implemented method of designing a wellbore isolation barrier, comprising inputting, by an analysis application executing on a computer system, a first set of inputs into a first model, wherein the first model is a computational fluid dynamics (CFD) model, wherein the first set of inputs comprises a cement blend, a one or more customer inputs, and a one or more injection schedule, inputting, by the analysis application, a second set of inputs into a second model, wherein the second model is a geochemistry model, wherein the second set of inputs comprises a first output from the first model, inputting, by the analysis application, a third set of inputs into a third model, wherein the third model is a mechanical property model, wherein the third set of inputs comprises a second output from the second model, determining, by the analysis application, a near wellbore stress state from an input, wherein the input comprises a third output from the third model, the first output from the first model, a set of user inputs, or combination thereof, comparing, by the analysis application, a failure property of at least one of i) rock, ii) cement, iii) casing, iv) or combination thereof, to the near wellbore stress state, modifying, by the analysis application, the injection schedule in response to the near wellbore stress state exceeding at least one threshold of the failure property of at least one of i) rock, ii) cement, iii) casing, iv) or combination thereof, and generating, by the analysis application, the injection schedule in response to the threshold exceeding the near wellbore stress state.

A ninth embodiment, which is the method of the eighth embodiment, further comprising retrieving, by an analysis application, the cement blend, the one or more customer inputs, and the injection schedule from a remote data source by a first communication method, wherein the injection schedule comprises a periodic carbon dioxide ($CO_2$) injection pressure and flowrate values.

A tenth embodiment, which is the method of any of the eighth and the ninth embodiments, wherein the one or more customer inputs comprise a plurality of wellbore data and a plurality of customer design inputs.

An eleventh embodiment, which is the method of the tenth embodiment, wherein the wellbore data comprises a wellbore location, a wellbore history, and a plurality of sensor data, wherein the wellbore location comprises well names, a lease location, global positioning satellite (GPS) coordinates, an internal designation, or a combination thereof, wherein the wellbore history comprises a wellbore survey, a wellbore drilling path, a wellbore production fluid analysis, a wellbore drilling fluid, the cement blend, and a wellbore construction history, and wherein the plurality of sensor data comprises well logging, wellbore production sample, and well control data.

A twelfth embodiment, which is the method of any of the eighth through the eleventh embodiments, further comprising returning, by the analysis application, to the first model, in response to the near wellbore stress state exceeding the at least one threshold, a modified set of inputs comprising the injection schedule.

A thirteenth embodiment, which is the method of any of the eighth through the twelfth embodiments, further comprising transmitting the injection schedule to an $CO_2$ injection equipment at a wellsite in response to the generation of the injection schedule, wherein the $CO_2$ injection equipment comprises a unit controller, and wherein the unit controller comprises a processor and non-transitory memory.

A fourteenth embodiment, which is the method of the thirteenth embodiment, further comprising pumping a supply of $CO_2$, by the $CO_2$ injection equipment, per the injection schedule by the unit controller, and retrieving, by the unit controller, one or more datasets of periodic $CO_2$ injection operation indicative of the injection schedule.

A fifteenth embodiment, which is the method of any of the eighth through the fourteenth embodiments, further comprising evaluating, by the analysis application, a near wellbore stress state for a wellbore isolation barrier to maintain a mechanical properties of i) a porous formation, ii) the wellbore isolation barrier, iii) the casing, or iv) combinations thereof by reducing the near wellbore stress state below a threshold by modifying an application of the injection schedule by an injection equipment.

A sixteenth embodiment, which is a computer-implemented method of designing a wellbore isolation barrier, comprising inputting, by an analysis application, a first set of inputs into a first model, wherein the first model is a computational fluid dynamics (CFD) model, wherein the first set of inputs comprises a wellbore cement blend, a one or more customer inputs, and a future injection schedule, inputting, by the analysis application, a second set of inputs into a second model, wherein the second model is a geochemistry model, wherein the second set of inputs comprises a first output from the first model, inputting, by the analysis application, a third set of inputs into a third model, wherein the third model is a mechanical property model, wherein the third set of inputs comprises a second output from the second model, calculating, by the analysis application, a future near wellbore stress state from a set of inputs, wherein the set of inputs comprises a third output from the third model, the first output from the first model, a set of user inputs, a current stress state, or combinations thereof, comparing, by the analysis application, a failure property of at least one of i) rock, ii) cement, iii) casing, iv) or combination thereof, to the future near wellbore stress state, modifying, by the analysis application, the future injection schedule in response to the future near wellbore stress state exceeding the failure property of at least one of i) rock, ii) cement, iii) casing, iv) or combination thereof, and generating, by the analysis application, the future injection schedule, in response to a threshold of the future near wellbore stress state exceeding the failure property of at least one of i) rock, ii) cement, iii) casing, iv) or combination thereof.

A seventeenth embodiment, which is the method of the sixteenth embodiment, further comprising retrieving, by an analysis application executing on a computer system, a present near wellbore stress state, a one or more customer inputs, a wellbore cement blend, and a future injection schedule from a remote data source by a first communication method, wherein the future injection schedule comprises periodic carbon dioxide ($CO_2$) injection pressure and flow-rate data.

An eighteenth embodiment, which is the method of any of the sixteenth and the seventeenth embodiments, wherein the one or more customer inputs comprise a plurality of wellbore data and a plurality of customer design inputs.

A nineteenth embodiment, which is the method of the eighteenth embodiment, wherein the wellbore data comprises a wellbore location, a wellbore history, and a plurality of sensor data, wherein the wellbore location comprises well names, a lease location, global positioning satellite (GPS) coordinates, an internal designation, or a combination thereof, wherein the wellbore history comprises a wellbore survey, a wellbore drilling path, a wellbore production fluid analysis, a wellbore drilling fluid, the wellbore cement blend, and a wellbore construction history, and wherein the plurality of sensor data comprises well logging, wellbore production sample, and well control data.

A twentieth embodiment, which is the method of any of the sixteenth through the nineteenth embodiments, further comprising transmitting the future injection schedule to $CO_2$ injection equipment at a wellsite in response to the generation of the future injection schedule, wherein the $CO_2$ injection equipment comprises a unit controller, and wherein the unit controller comprises a processor and non-transitory memory, pumping a $CO_2$ supply, by the $CO_2$ injection equipment, per the future injection schedule by the unit controller, and retrieving, by the unit controller, one or more datasets of periodic $CO_2$ injection data indicative of the future injection schedule.

A twenty-first embodiment, which is a method comprising evaluating a near wellbore stress state for a wellbore isolation barrier in accordance with any of the first through the twentieth embodiments to design a mechanical properties of a cement blend of the wellbore isolation barrier below a threshold value of the near wellbore stress state, constructing a wellbore with the cement blend, wherein the cement blend transforms into the wellbore isolation barrier upon curing, evaluating the near wellbore stress state to determine a near wellbore stress of the wellbore isolation barrier by a process comprising inputting, by an analysis application, a first set of inputs into a first model, wherein the first model is a computational fluid dynamics (CFD) model, wherein the first set of inputs comprises the cement blend, the one or more customer inputs, and the injection schedule, inputting, by the analysis application, a second set of inputs into a second model, wherein the second model is a geochemistry model, wherein the second set of inputs comprises a first output from the first model, inputting, by the analysis application, a third set of inputs into a third model, wherein the third model is a mechanical property model, wherein the third set of inputs comprises a second output from the second model, calculating, by the analysis application, a future near wellbore stress state from a set of inputs, wherein the set of inputs comprises a third output from the third model, the first output from the first model, set of user inputs, or combination thereof, comparing, by the analysis application, a failure property of at least one of i) rock, ii) cement, iii) casing, iv) or combination thereof, to the future near wellbore stress state, and generating, by the analysis application, the future injection schedule, in response to a threshold of a future near wellbore stress state exceeding failure property of at least one of i) rock, ii) cement, iii) casing, iv) or combination thereof, and injecting carbon dioxide ($CO_2$), by an injection equipment, per the future injection schedule in response to the injection schedule producing a near wellbore stress below the threshold value, and modifying the future injection schedule in response to evaluating the near wellbore stress state of the wellbore isolation barrier to lower the near wellbore stress below the threshold value by a process comprising inputting, by an analysis application, a first set of inputs into a first model, wherein the first model is a CFD model, wherein the first set of inputs comprises the wellbore cement blend, a one or more customer inputs, and the future injection schedule, inputting, by the analysis application, a second set of inputs into a second model, wherein the second model is a geochemistry model, wherein the second set of inputs comprises a first output from the first model, inputting, by the analysis application, a third set of inputs into a third model, wherein the third model is a mechanical property model, wherein the third set of inputs comprises a second output from the second model, calculating, by the analysis application, a future near wellbore stress state from a set of inputs, wherein the set of inputs comprises a third output from the third model, the first output from the first model, a set of user inputs, or combination thereof, comparing, by the analysis application, a failure property of at least one of i) rock, ii) cement, iii) casing, iv) or combination thereof, to the future near wellbore stress state, and modifying, by the analysis application, the future injection schedule in response to the future near wellbore stress state exceeding the failure property of at least one of i) rock, ii) cement, iii) casing, iv) or combination thereof.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method comprising:
   designing a designed cement blend, a designed injection schedule or a combination thereof for a wellbore isolation barrier, wherein the designing is performed using instructions stored in at least one non-transitory memory that, when executed by one or more processors, configure the one or more processors to perform a method comprising:
   (i) inputting, by an analysis application, a first set of inputs into a first model, wherein the first model is a computational fluid dynamics (CFD) model, and wherein the first set of inputs comprises a cement blend, one or more customer inputs, and an injection schedule;
   (ii) inputting, by the analysis application, a second set of inputs into a second model, wherein the second model is a geochemistry model, wherein the second set of inputs comprises a first output from the first model;
   (iii) inputting, by the analysis application, a third set of inputs into a third model, wherein the third model is a mechanical property model, wherein the third set of inputs comprises a second output from the second model;
   (iv) determining, by the analysis application, a near wellbore stress state from an input, wherein the input comprises a third output from the third model, the first output from the first model, a set of user inputs, or combination thereof;
   (v) comparing, by the analysis application, a failure property threshold of at least one of i) rock, ii) cement, iii) casing, iv) or combination thereof, to the near wellbore stress state; and either:
   (vi)(a) in response to the near wellbore stress state exceeding the failure property threshold, modifying, by the analysis application, the cement blend, the injection schedule, or combination thereof to provide a modified cement blend, a modified injection schedule, or both and returning to step (i) wherein the cement blend, the injection schedule, or both are updated with the modified cement blend, the modified injection schedule, or both, respectively, or
   (vi)(b) in response to the near wellbore stress state not exceeding the failure property threshold, generating, by the analysis application, the designed cement blend, the designed injection schedule, or combination thereof for the wellbore isolation barrier.

2. The method of claim 1, further comprising:
   retrieving, by the analysis application, the first set of inputs from a remote data source by a first communication method.

3. The method of claim 1, wherein the mechanical property model is a cement mechanical model, a rock mechanical model, or combination thereof.

4. A method comprising:
   evaluating a near wellbore stress state for a wellbore isolation barrier in accordance with claim 1 to provide the designed cement blend;
   constructing a wellbore with a cement slurry comprising the design cement blend, wherein the cement slurry transforms into the wellbore isolation barrier upon curing;
   evaluating the near wellbore stress state to determine a near wellbore stress of the wellbore isolation barrier, wherein the evaluating is performed using instructions stored in the at least one non-transitory memory that, when executed by one or more processors, configure the one or more processors to perform a method comprising:
   (i) inputting, by an analysis application, a first set of inputs into a first model, wherein the first model is a computational fluid dynamics (CFD) model, wherein the first set of inputs comprises the cement blend, the one or more customer inputs, and the injection schedule;
   (ii) inputting, by the analysis application, a second set of inputs into a second model, wherein the second model is a geochemistry model, wherein the second set of inputs comprises a first output from the first model;
   (iii) inputting, by the analysis application, a third set of inputs into a third model, wherein the third model is a mechanical property model, wherein the third set of inputs comprises a second output from the second model;
   (iv) calculating, by the analysis application, a future near wellbore stress state from a set of inputs, wherein the set of inputs comprises a third output from the third model, the first output from the first model, set of user inputs, or combination thereof;
   (v) comparing, by the analysis application, a failure property threshold of at least one of i) rock, ii) cement, iii) casing, iv) or combination thereof, to the future near wellbore stress state; and either:
   (vi)(a) in response to the future near wellbore stress state exceeding the failure property threshold of at least one of i) rock, ii) cement, iii) casing, iv) or combination thereof, modifying, by the analysis application, the injection schedule to provide a modified injection schedule and returning to step (i) wherein the injection schedule is replaced with the modified injection schedule; or
   (vi)(b) in response to the future near wellbore stress state not exceeding the failure property threshold of at least one of i) rock, ii) cement, iii) casing, iv) or combination thereof, generating, by the analysis application, a future injection schedule for the wellbore isolation barrier, and injecting carbon dioxide ($CO_2$), by an injection equipment, per the future injection schedule.

5. The method of claim 1, wherein:
   the injection schedule comprises periodic carbon dioxide ($CO_2$) injection pressure, temperature, and flowrate values; and
   wherein the one or more customer inputs comprise a plurality of wellbore data and a plurality of customer design inputs comprising a bill of materials and one or more construction plans.

6. The method of claim 5, wherein:
   the wellbore data comprises a wellbore location, a wellbore history, a plurality of sensor data, or combination thereof;
   wherein the wellbore location comprises well names, a lease location, global positioning satellite (GPS) coordinates, an internal designation, or combination thereof;
   wherein the wellbore history comprises a wellbore survey, a wellbore drilling path, a wellbore production fluid analysis, a wellbore drilling fluid, a wellbore construction history, or combination thereof; and
   wherein the plurality of sensor data comprises well logging, wellbore production sample, well control data, or combination thereof.

7. The method of claim 1, further comprising:

transporting a cement composition comprising the designed cement blend and a plurality of cement pumping equipment to a well site in response to an output of the designed cement blend, wherein the cement composition is included in a cement placement procedure, wherein the cement pumping equipment comprise a unit controller;

connecting the cement pumping equipment to a wellbore via a wellhead, wherein the pumping equipment is fluidically connected to the wellbore;

beginning the cement placement procedure by the unit controller;

retrieving, by the unit controller, one or more datasets of periodic pumping data indicative of the cement placement procedure;

mixing a cement slurry comprising the cement composition, by the cement pumping equipment, per the cement placement procedure; and pumping the cement slurry per the cement placement procedure into the wellbore.

8. The method of claim 7, further comprising:

evaluating, by the analysis application, the near wellbore stress state for a wellbore isolation barrier to maintain at least one mechanical property of i) a porous formation, ii) the wellbore isolation barrier, iii) the casing, or iv) combinations thereof by reducing the near wellbore stress state below a threshold by modifying an application of the designed injection schedule by an injection equipment.

9. A method comprising:

designing a designed injection schedule for a wellbore isolation barrier, wherein the designing is performed using instructions stored in the at least one non-transitory memory that, when executed by one or more processors, configure the one or more processors to perform a method comprising:

(i) inputting, by an analysis application executing on a computer system, a first set of inputs into a first model, wherein the first model is a computational fluid dynamics (CFD) model, wherein the first set of inputs comprises a cement blend, one or more customer inputs, and an injection schedule;

(ii) inputting, by the analysis application, a second set of inputs into a second model, wherein the second model is a geochemistry model, wherein the second set of inputs comprises a first output from the first model;

(iii) inputting, by the analysis application, a third set of inputs into a third model, wherein the third model is a mechanical property model, wherein the third set of inputs comprises a second output from the second model;

(iv) determining, by the analysis application, a near wellbore stress state from an input, wherein the input comprises a third output from the third model, the first output from the first model, a set of user inputs, or combination thereof;

(v) comparing, by the analysis application, a failure property threshold of at least one of i) rock, ii) cement, iii) casing, iv) or combination thereof, to the near wellbore stress state; and either:

(vi)(a) in response to the near wellbore stress state exceeding the failure property threshold of at least one of i) rock, ii) cement, iii) casing, iv) or combination thereof, modifying, by the analysis application, the injection schedule to provide a modified injection schedule and returning to step (i) wherein the injection schedule is updated with the modified injection schedule; or (vi)(b) in response to the near wellbore stress state not exceeding the failure property threshold of at least one of i) rock, ii) cement, iii) casing, iv) or combination thereof, generating, by the analysis application, the designed injection schedule for the wellbore isolation barrier.

10. The method of claim 9, further comprising:

retrieving, by an analysis application, the cement blend, the one or more customer inputs, and the injection schedule from a remote data source by a first communication method, wherein the injection schedule comprises a periodic carbon dioxide ($CO_2$) injection pressure and flowrate values.

11. The method of claim 9, wherein:

the one or more customer inputs comprise a plurality of wellbore data and a plurality of customer design inputs.

12. The method of claim 11, wherein:

the wellbore data comprises a wellbore location, a wellbore history, and a plurality of sensor data, wherein the wellbore location comprises well names, a lease location, global positioning satellite (GPS) coordinates, an internal designation, or a combination thereof;

wherein the wellbore history comprises a wellbore survey, a wellbore drilling path, a wellbore production fluid analysis, a wellbore drilling fluid, the cement blend, and a wellbore construction history; and wherein the plurality of sensor data comprises well logging, wellbore production sample, and well control data.

13. The method of claim 9, further comprising:

transmitting the designed injection schedule to an $CO_2$ injection equipment at a wellsite in response to the generation of the designed injection schedule, wherein the $CO_2$ injection equipment comprises a unit controller, and wherein the unit controller comprises a processor and non-transitory memory.

14. The method of claim 13, further comprising:

pumping a supply of $CO_2$, by the $CO_2$ injection equipment, per the design injection schedule by the unit controller; and retrieving, by the unit controller, one or more datasets of periodic $CO_2$ injection operation indicative of the designed injection schedule.

15. The method of claim 14, further comprising:

evaluating, by the analysis application, a near wellbore stress state for a wellbore isolation barrier to maintain at least one mechanical property of i) a porous formation, ii) the wellbore isolation barrier, iii) the casing, or iv) combinations thereof by reducing the near wellbore stress state below a threshold by modifying an application of the designed injection schedule by an injection equipment.

16. A method comprising:

designing a designed future injection schedule for a wellbore isolation barrier, wherein the designing is performed using instructions stored in at least one non-transitory memory that, when executed by one or more processors, configure the one or more processors to perform a method comprising:

(i) inputting, by an analysis application, a first set of inputs into a first model, wherein the first model is a computational fluid dynamics (CFD) model, wherein the first set of inputs comprises a wellbore cement blend, one or more customer inputs, and a future injection schedule;

(ii) inputting, by the analysis application, a second set of inputs into a second model, wherein the second model is a geochemistry model, wherein the second set of inputs comprises a first output from the first model;

(iii) inputting, by the analysis application, a third set of inputs into a third model, wherein the third model is a mechanical property model, wherein the third set of inputs comprises a second output from the second model;

(iv) calculating, by the analysis application, a future near wellbore stress state from a set of inputs, wherein the set of inputs comprises a third output from the third model, the first output from the first model, a set of user inputs, a current stress state, or combinations thereof;

(v) comparing, by the analysis application, a failure property threshold of at least one of i) rock, ii) cement, iii) casing, iv) or combination thereof, to the future near wellbore stress state; and either:

(vi)(a) in response to the future near wellbore stress state exceeding the failure property threshold of at least one of i) rock, ii) cement, iii) casing, iv) or combination thereof, modifying, by the analysis application, the future injection schedule to provide a modified future injection schedule and returning to step (i) wherein the future injection schedule is replaced with the modified future injection schedule; or (vi)(b) in response to the future near wellbore stress state not exceeding the failure property threshold of at least one of i) rock, ii) cement, iii) casing, iv) or combination thereof, generating, by the analysis application, the designed future injection schedule for the wellbore isolation barrier.

17. The method of claim 16, further comprising:
retrieving, by an analysis application executing on a computer system, a present near wellbore stress state, the one or more customer inputs, the wellbore cement blend, and the future injection schedule from a remote data source by a first communication method, wherein the future injection schedule comprises periodic carbon dioxide ($CO_2$) injection pressure and flowrate data.

18. The method of claim 16, wherein:
the one or more customer inputs comprise a plurality of wellbore data and a plurality of customer design inputs.

19. The method of claim 18, wherein:
the wellbore data comprises a wellbore location, a wellbore history, and a plurality of sensor data, wherein the wellbore location comprises well names, a lease location, global positioning satellite (GPS) coordinates, an internal designation, or a combination thereof;
wherein the wellbore history comprises a wellbore survey, a wellbore drilling path, a wellbore production fluid analysis, a wellbore drilling fluid, the wellbore cement blend, and a wellbore construction history; and
wherein the plurality of sensor data comprises well logging, wellbore production sample, and well control data.

20. The method of claim 16, further comprising:
transmitting the designed future injection schedule to $CO_2$ injection equipment at a wellsite in response to the generation of the designed future injection schedule, wherein the $CO_2$ injection equipment comprises a unit controller, and wherein the unit controller comprises a processor and non-transitory memory;
pumping a $CO_2$ supply, by the $CO_2$ injection equipment, per the designed future injection schedule by the unit controller; and
retrieving, by the unit controller, one or more datasets of periodic $CO_2$ injection data indicative of the designed future injection schedule.

21. The method of claim 20, further comprising:
evaluating, by the analysis application, a near wellbore stress state for a wellbore isolation barrier to maintain at least one mechanical property of i) a porous formation, ii) the wellbore isolation barrier, iii) the casing, or iv) combinations thereof by reducing the near wellbore stress state below a threshold by modifying an application of the designed future injection schedule by the injection equipment.

* * * * *